United States Patent [19]
Raviv et al.

[11] Patent Number: 5,671,733
[45] Date of Patent: Sep. 30, 1997

[54] METHOD OF ANALYZING SLEEP DISORDERS

[75] Inventors: Gil Raviv, Northbrook; Charles Z. Weingarten, Wilmette, both of Ill.

[73] Assignee: SNAP Laboratories, L.L.C., Glenview, Ill.

[21] Appl. No.: 231,025

[22] Filed: Apr. 21, 1994

[51] Int. Cl.$^6$ .................................................. A61B 5/00
[52] U.S. Cl. .................... 128/630; 128/671; 128/716
[58] Field of Search ........................ 128/630, 715–716, 128/773–4, 848, 670–1

[56] References Cited

U.S. PATENT DOCUMENTS

| | | |
|---|---|---|
| 3,593,703 | 7/1971 | Gunn . |
| 4,715,367 | 12/1987 | Crossley ........................ 128/774 X |
| 4,802,485 | 2/1989 | Bowers . |
| 4,848,360 | 7/1989 | Palsgard et al. .................... 128/773 |
| 4,982,738 | 1/1991 | Griebel . |
| 5,199,424 | 4/1993 | Sullivan . |
| 5,245,995 | 9/1993 | Sullivan . |
| 5,265,624 | 11/1993 | Bowman ........................ 128/724 X |
| 5,275,159 | 1/1994 | Griebel . |

OTHER PUBLICATIONS

How to Identify the Soft Palate Snorer and Predict Success of UPPP Laryngo–Rhino–Ocol. 69 (1989) [at pp. 290–295].
The Importance of Snoring in the Diagnostic Evaluation of Sleep–Related Disturbances . . . Prax. Klin. Pneumol 41 (1987) [at pp. 375–379].

Digital Signal Analysis of Snoring Sounds in Children Internat'l Journal of Pedriatic Otorhinolaryngology 20 (1990) [at pp. 193–202].

Characteristics of the Snoring Noise in Patients with and without occlusive sleep APNEA American Review of Respiratory Disease, vol. 147 (1993) [at pp. 635–644].

Automated APNOEA Detection by Computer Analysis of Tracheal Breath Sounds Medical & Biological Engineering & Computering (Sep. 1983) [at pp. 632–635].

*Primary Examiner*—John P. Lacyk
*Attorney, Agent, or Firm*—Welsh & Katz, Ltd.

[57] ABSTRACT

The invention provides a method of detecting, analyzing sleep disorders. The method includes the step of monitoring sound produced by a sleeping subject through a sensor proximate the sleeping subject and continuously recording the monitored sound. The method further includes identifying snoring within the recorded sound and analyzing the identified snoring to localize upper airway structural sources of snoring.

25 Claims, 10 Drawing Sheets

Microfiche Appendix Included
(1 Microfiche, 21 Pages)

FIG. 6B — SEPARATING SNORES FROM OTHER RESPIRATORY EVENTS

METHOD OF ANALYZING SLEEP DISORDERS (A microfiche appendix is included that consists of 1 microfiche, 21 pages, 21 frames.)

The present invention relates to sleep disorders and in particular to methods and apparatus for analyzing snoring and apnea.

BACKGROUND

An awareness of the risks of sleep disorders in recent years has prompted a number of discoveries associated with sleep apnea and snoring. Sleep apnea is a known factor associated with heart problems.

Sleep apnea is generally regarded as an interruption in the breathing pattern of a sleeping subject. Interruptions of a breathing pattern may be spontaneous or may result from a breathing obstruction such as a sleeping subject's tongue blocking the airway or from partial or complete upper airway occlusion where the upper airway collapses, particularly under the reduced pressure generated by inhalation. Obstructive sleep apnea may result in lowered arterial blood oxygen levels and poor quality of sleep.

It is estimated that there are more than 40 million chronic snorers in the United States. Snoring is often a factor associated with sleep apnea. In addition to heart problems, sleeping disorders degrade the quality of rest for a person with the sleeping disorder as well as other people, such as a spouse, sharing the sleeping quarters.

Prior art efforts to provide data relative to sleep disorders have included the Sleep Apnea Monitor of U.S. Pat. No. 4,802,485. U.S. Pat. No. 4,804,485 provides a method of monitoring for sleep apnea that includes a number of sensors (blood-oxygen sensor, snoring sensor and head position sensor) mounted to headgear of a monitored subject. The sensors are, in turn, interconnected with a data logger for recording and subsequent analysis by a doctor or technician.

Other patents, such as U.S. Pat. No. 4,982,738, have included additional sensors for recording the time intervals between snoring events. Such advances have improved the content of the data recorded for later analysis by trained personnel.

Another advance, such as U.S. Pat. No. 5,275,159, have used a computer in conjunction with a data logger to improve the presentation of recorded data. The data logged under the invention of U.S. Pat. No. 5,274,159 could be presented under any of three possible formats: (1) as a graph of sensor value versus time; (2) as histograms and tables; and (3) as episodes per hour of a selected parameter.

While the prior art has offered a number of improvements in the technology associated with presenting recorded data, the final diagnosis of the source of the sleep disorder still lies with the attending physician.

The most common surgical procedure used by physicians for correcting sleep disorders such as apnea or snoring is uvulopalatopharnygoplasty ("UPPP"). Other procedures often used include adenoidectomy, tonsillectomy, septoplasty, turbinectomy, and polypectomy. In some cases physicians even perform surgery of the hypopharynx and tongue.

In the case of snoring, if the generation site of the snoring is below the plane of the uvula, then surgery becomes very complicated and, often, impractical. Also, although there is no definitive method for identifying sources of snoring, statistics show that UPPP reduces apnea 50% of the time and snoring 75–80% of the time. Because of the importance of the proper diagnosis of sleep disorders, a need exists for a simple and convenient method of determining the sources and types of sleep disorders that is not completely dependent upon the judgment and experience of an attending physician. It would be further advantageous to be able to easily identify the source of snoring to permit evaluation of the probability of success of the various surgical options.

SUMMARY OF THE INVENTION

In summary, the invention provides a method of analyzing sleep disorders. The method includes the step of monitoring sound produced by a sleeping subject through a sensor proximate the sleeping subject and continuously recording the monitored sound. The method further includes identifying snoring within the recorded sound and analyzing the identified snoring to locate upper airway structural sources of snoring.

BRIEF DESCRIPTION OF APPENDIX 1

Appendix 1 (see microfiche appendix) lists the source code routines of present invention. Table 1 (see microfiche appendix) provides key routines the corresponding to the processes depicted in FIGS. 5 and 6.

BRIEF DESCRIPTION OF APPENDIX 2

Figure 5A:
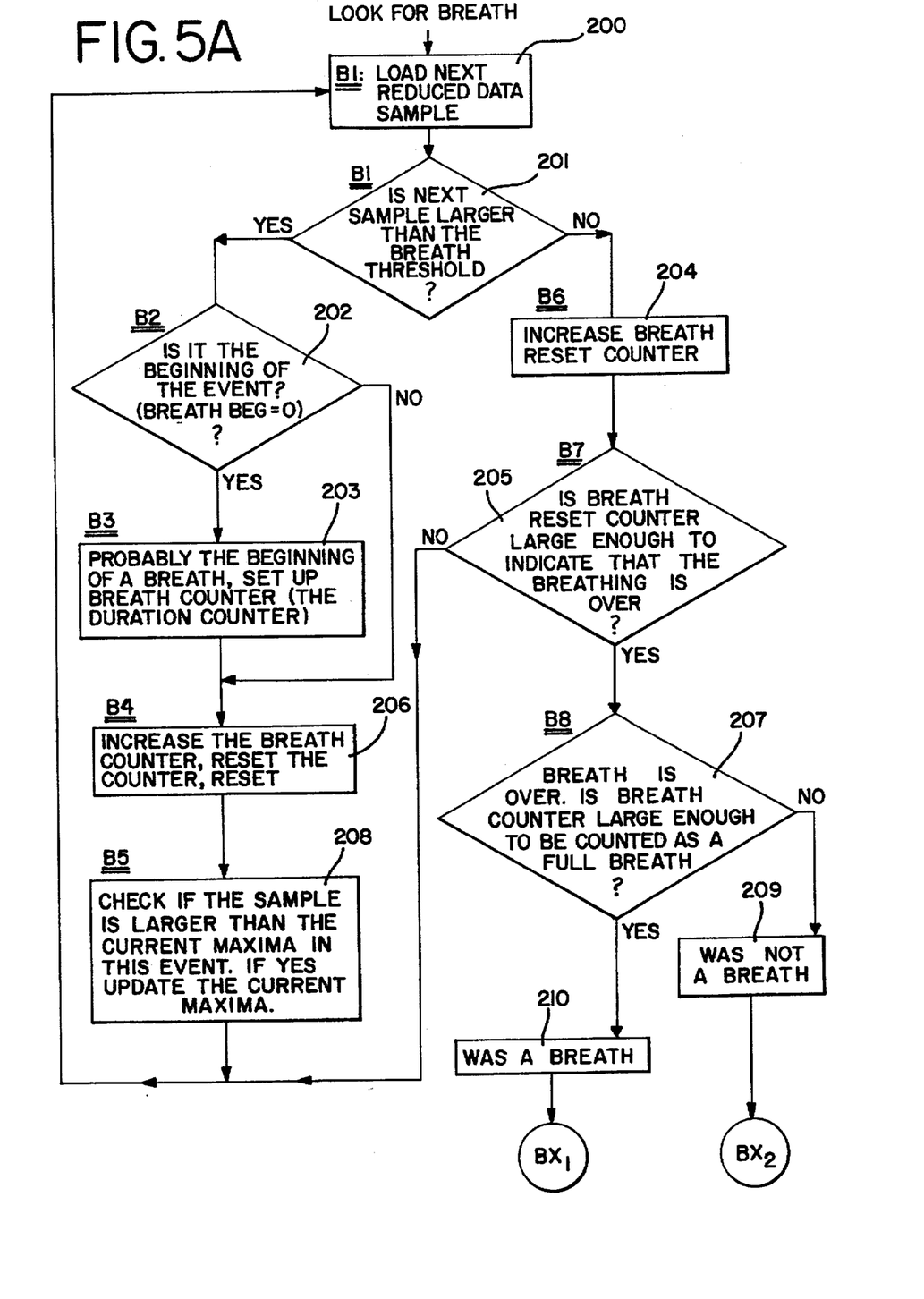
FIGS. 5A and 5B is a flow chart for breath detection in accordance with the invention.
Figure 5B:
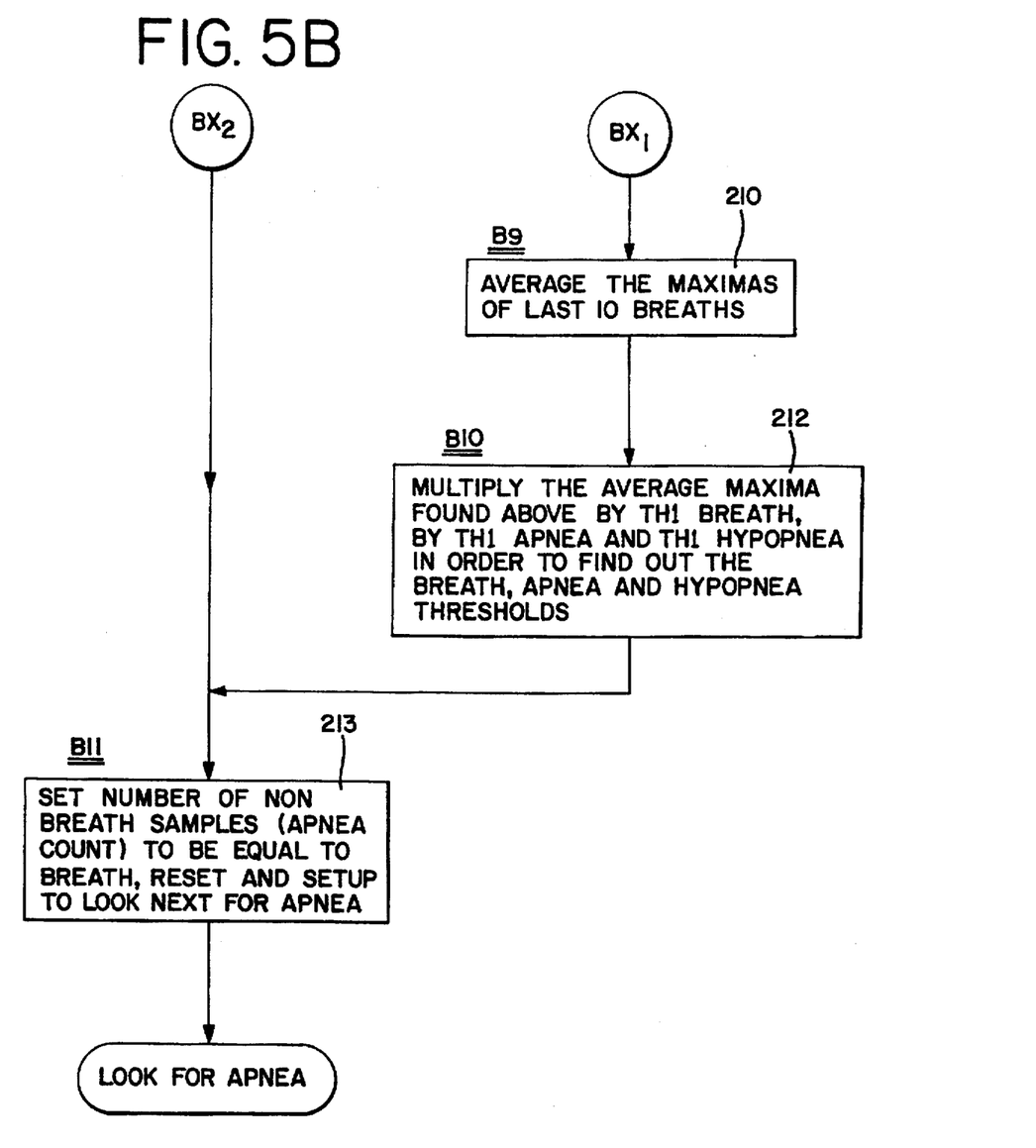
Figure 6A:
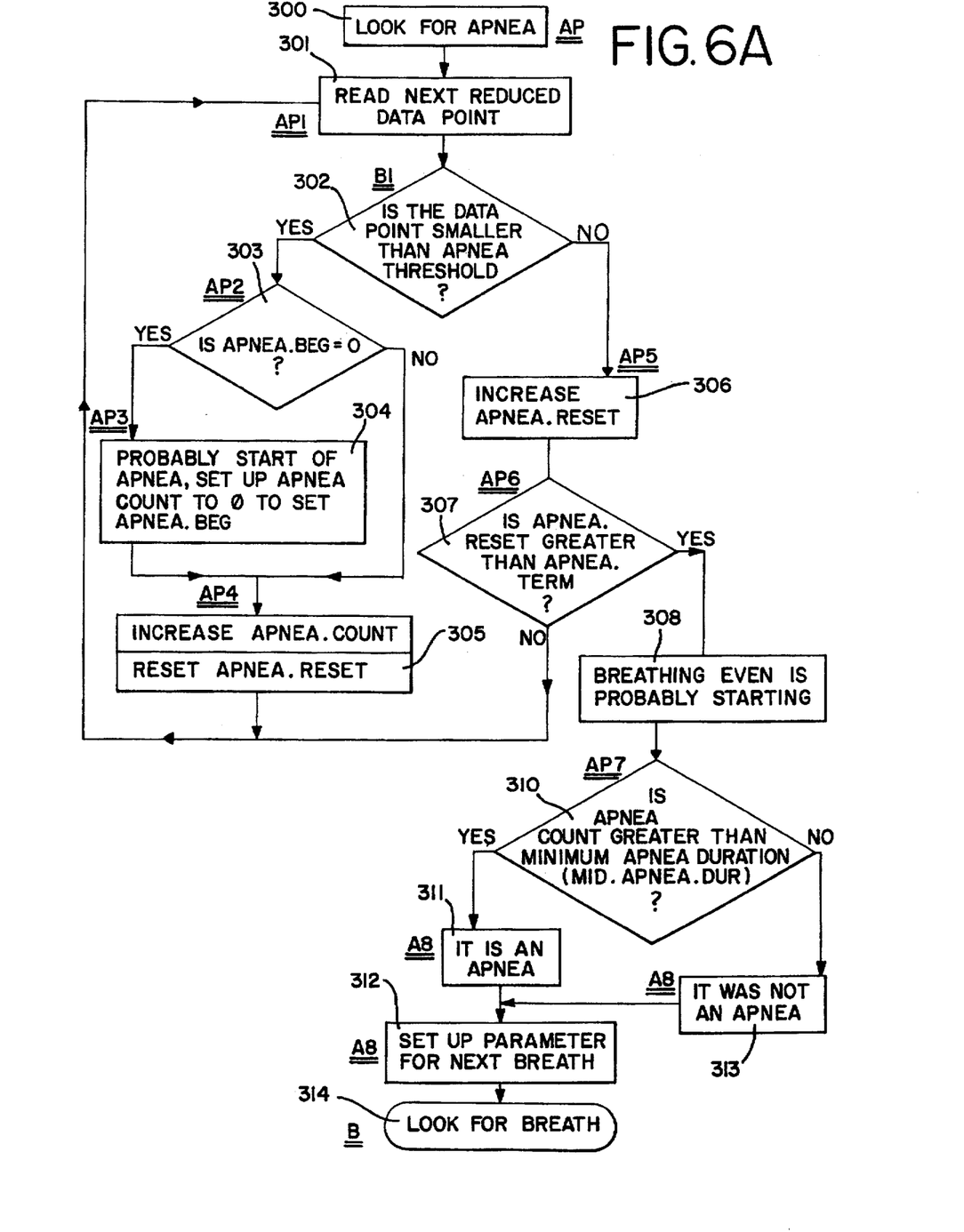
FIGS. 6A–6F is a flow chart of apnea/snoring analysis in accordance with the invention.
Figure 6B:
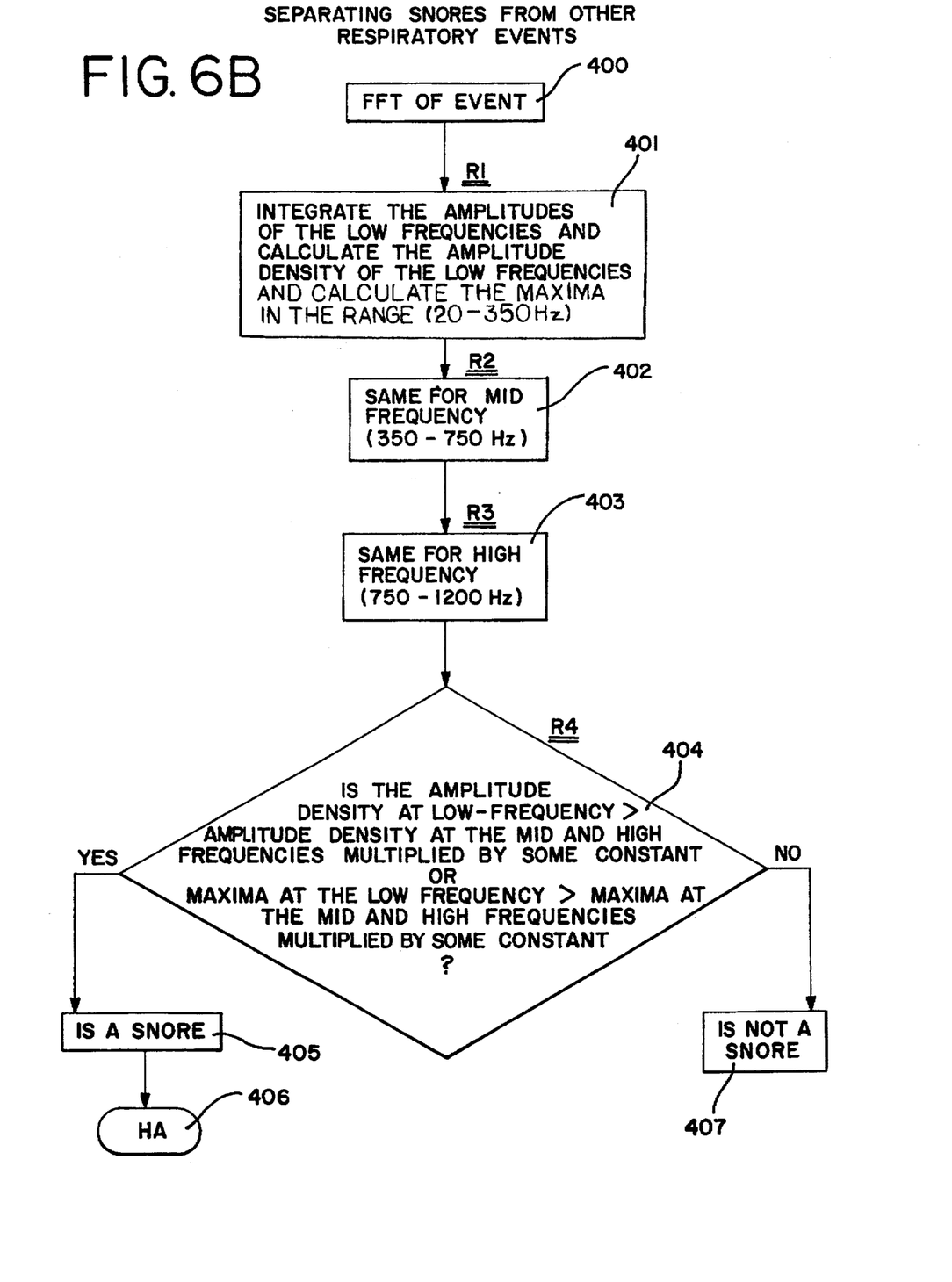
Figure 6C:
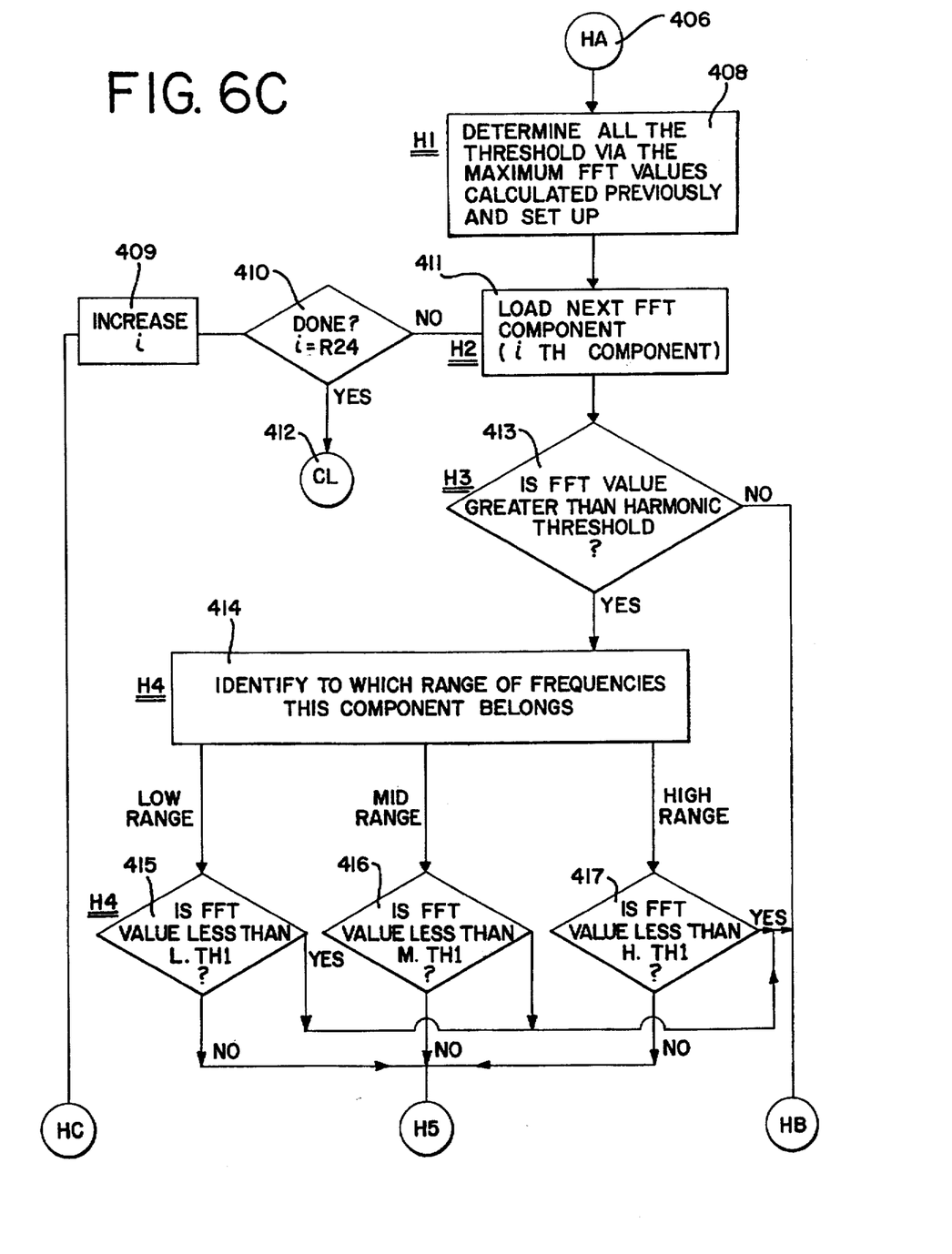
Figure 6D:
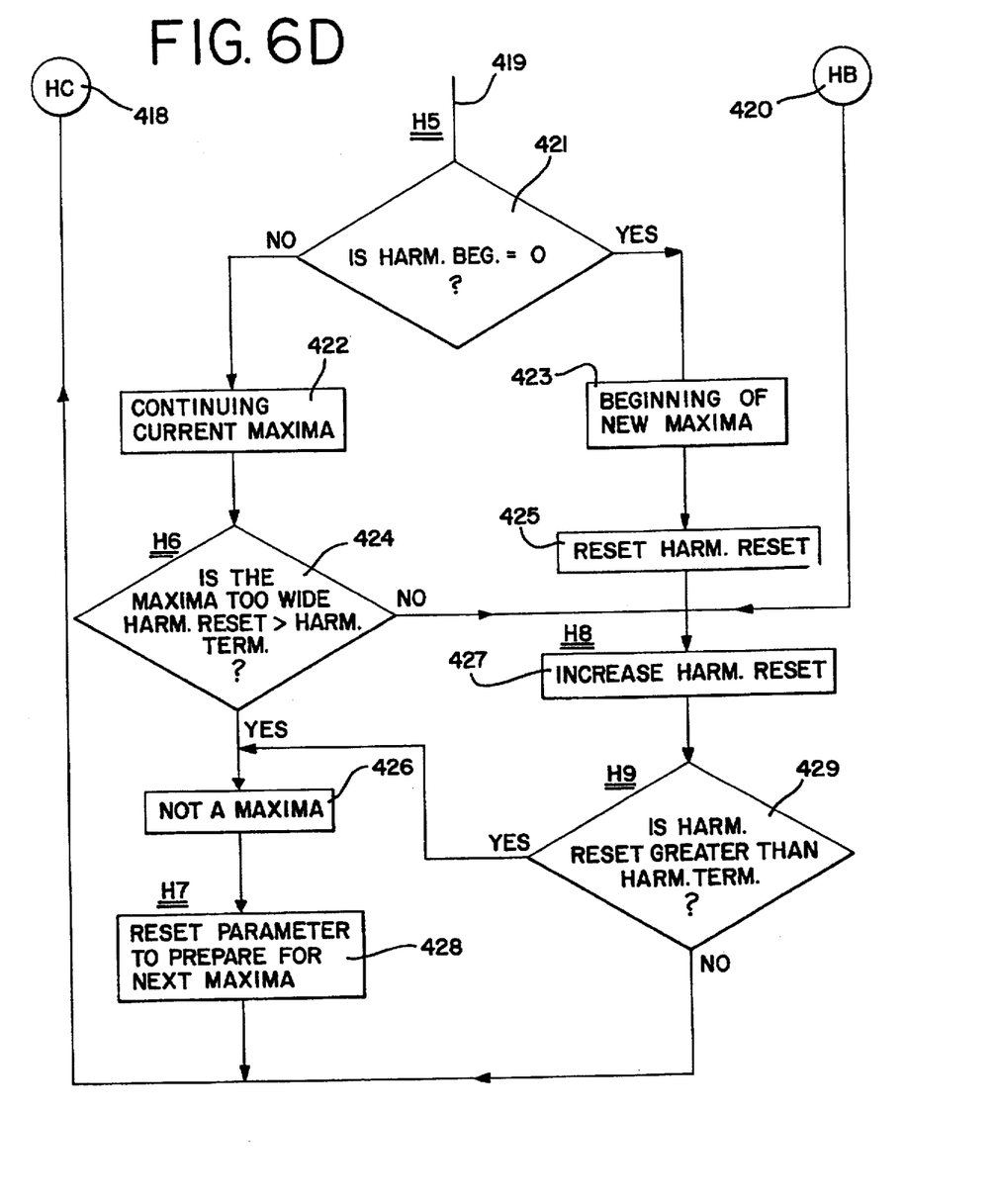
Figure 6E:
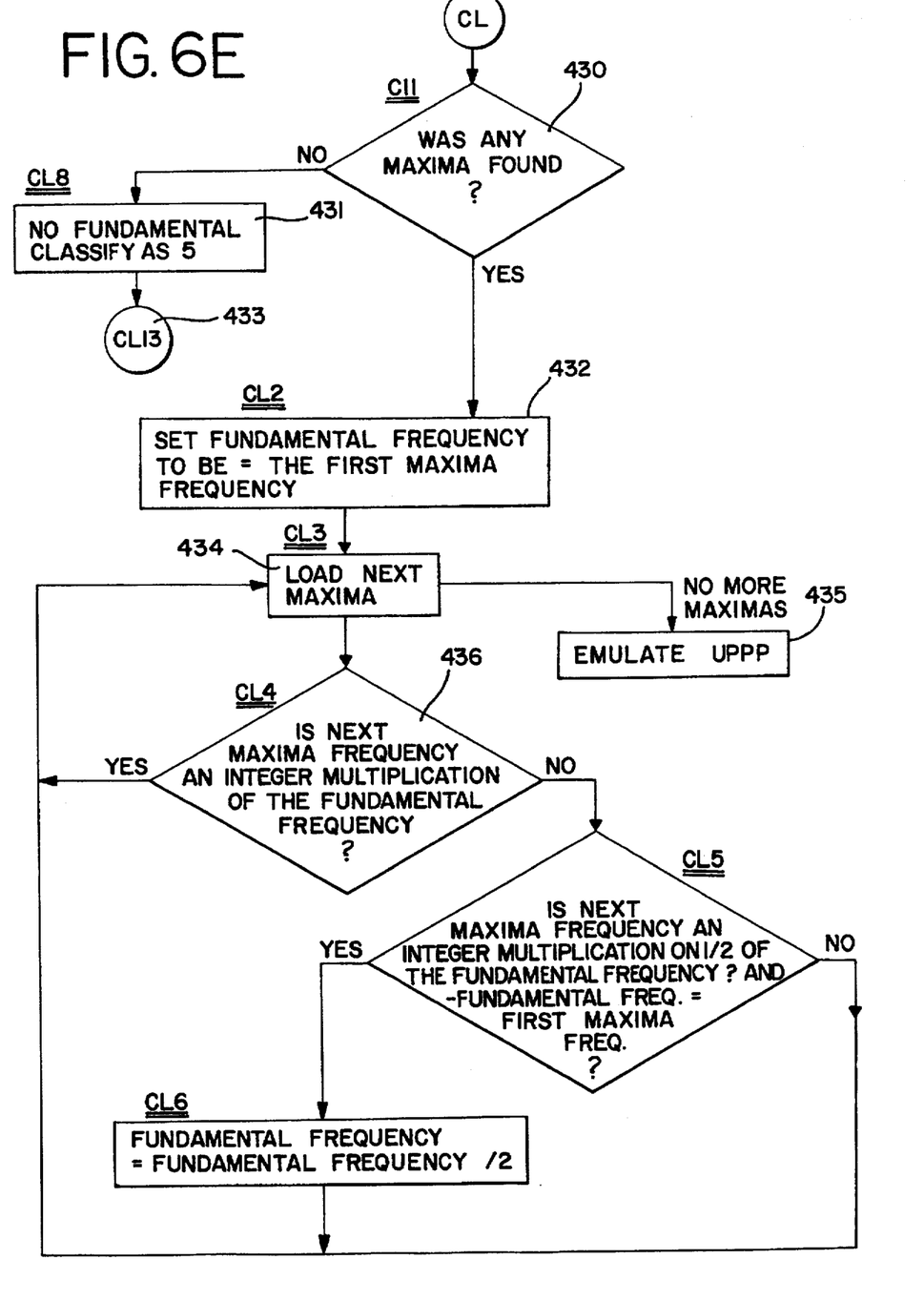
Figure 6F:
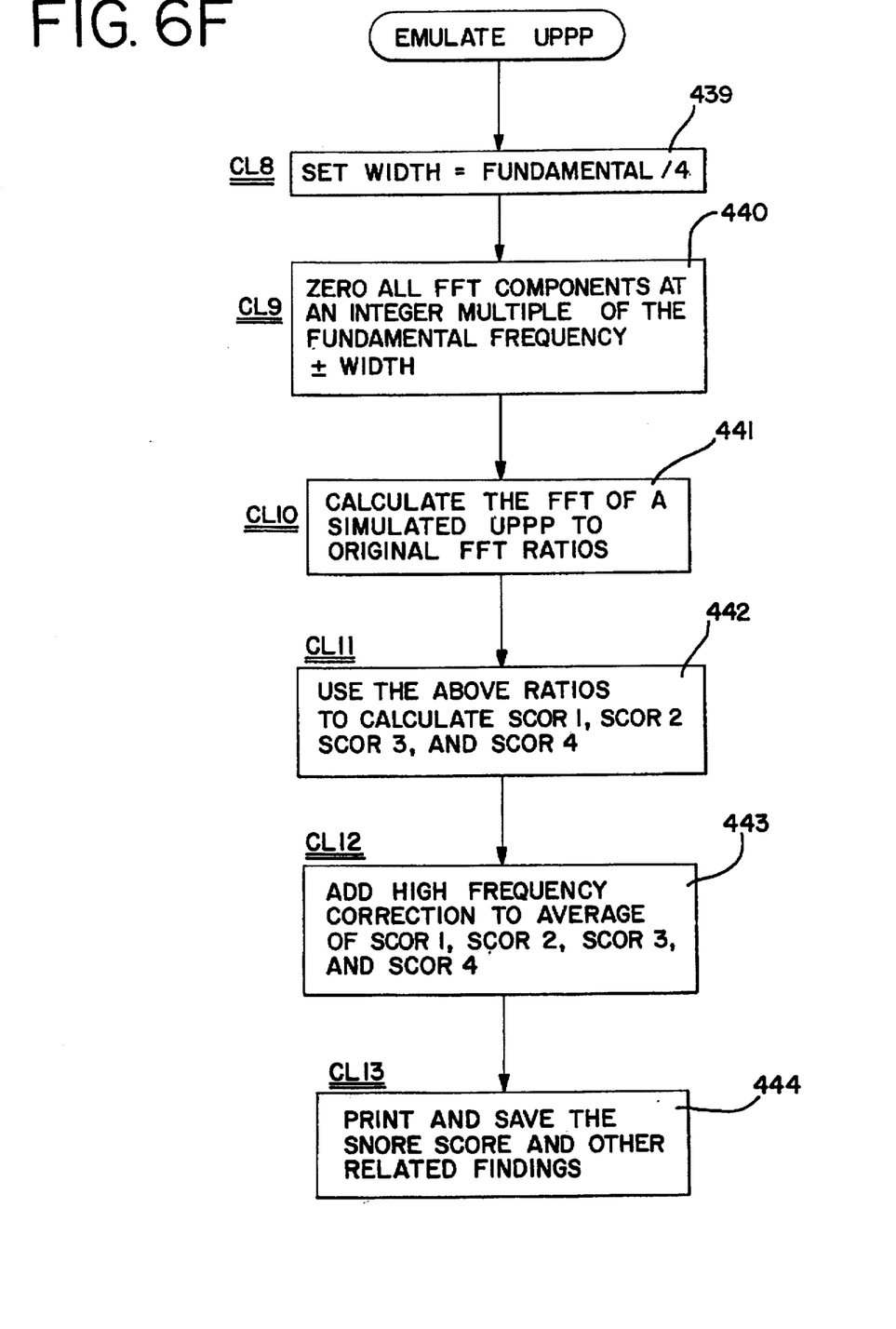

Appendix 2 (see microfiche appendix) contains a list of the text within FIGS. 5 and 6 along with references.

BRIEF DESCRIPTION OF THE PREFERRED EMBODIMENT

The solution to the problem of analyzing sleep disorders lies, conceptually, in data logging appropriate physiological characteristics (such as sound, body position, blood oxygen levels, et cetera) of a sleeping subject and using the logged data within a formalistic process to identify types and sources of sleep disorders. It has been determined that frequency content of snoring of most subjects will differ based upon the structural source within the upper airway causing the snoring. The frequency of snoring caused by the palate and uvula will differ, for example, from the frequency content of snoring caused by sites lower in the throat. Further determination that a sleeping subject snores through the subject's nose instead of the subject's mouth (or visa versa) may be used to eliminate certain structures as possible sources of the snoring.

The technique of analyzing sleep disorders provided under the invention localizes the source of the sleep disorder based upon information contained within the logged data. Under the invention, apnea and hypopnea are identified by comparison of characteristic parameters within the logged data with characteristic threshold values. Snoring, on the other hand, is analyzed by relating the frequency content of the snoring with upper airway structural sources. To identify structural sources, an analysis is performed within the frequency domain on an audio portion of the logged data to identify and measure fundamental frequencies and harmonics associated with the upper airway structures of the subject's breathing passages. It has been determined empirically that snoring sounds associated with structures such as the soft palate and uvula have fundamental frequencies that are typically in the range of from 20–300 Hertz while snoring originating from other structures (other than the throat) lie at higher frequencies. Throat snoring, while having frequencies in the range of from 20–300 Hz has a diffuse frequency content.

It has also been determined that snoring sounds emanating from nasal passages have higher fundamental frequencies than sounds originating from the mouth. Snoring sounds originating from the mouth, while lower in fundamental frequencies, are also somewhat more diffuse in frequency content.

The tonsils of some subjects have been determined to affect the fundamental frequency of snoring. Where the tonsils interfere with movement of the tongue and uvula, a fundamental frequency of greater than 130 Hz would be expected.

Figure 4:
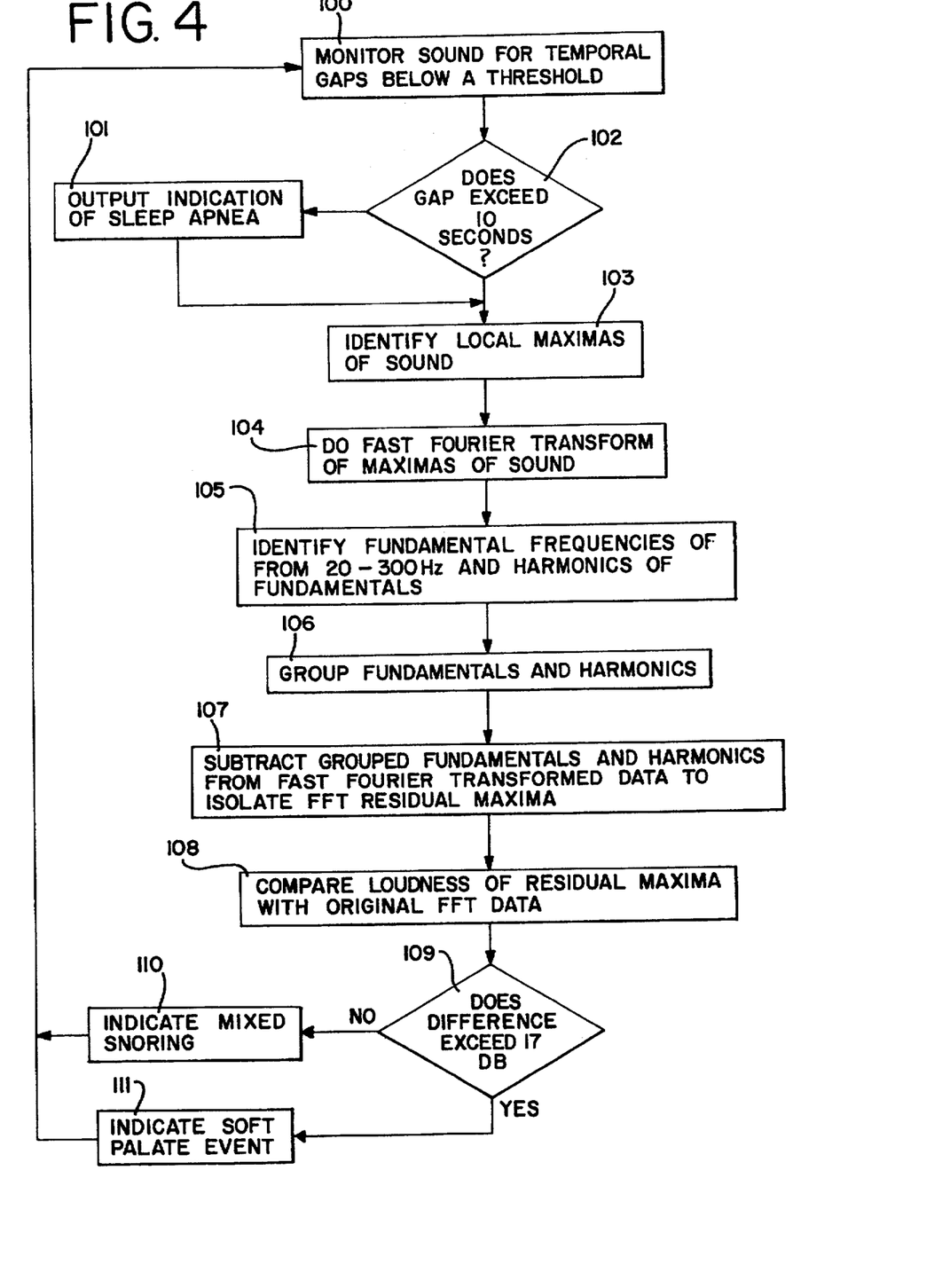
FIG. 4 is a flow chart of data analysis in accordance with the invention.

FIG. 4 is a flow chart describing the method used under an embodiment of the invention. Reference will be made to FIG. 4 as appropriate to provide an understanding of the invention. It is to be understood that under the invention some steps of the invention may be performed manually or the entire process of FIG. 4 may be executed automatically under the control of a general purpose computer.

To facilitate analysis of respiratory and snoring sounds, the data logged audio information is limited to a frequency range of from 0–1250 Hertz. Local maxima are then identified within the audio information as well as gaps in respiratory sounds exceeding 10 seconds. Where gaps in excess of 10 seconds are detected, an output is provided indicating possible apnea.

A frequency domain conversion [i.e., a fast fourier transform ("FFT")] is performed on the audio information. The fast fourier transformed audio information is then examined at the temporal locations of the previously identified local maxima. Where the results of the FFT at the sites of the local maxima indicate that the local maxima is predominantly made up of a fundamental frequency in the proper frequency range and multiples of the fundamental, a determination is made that the sleep disorder is a soft palate event associated with the palate and uvula (velum snore). Identification of the sleep disorder to be a soft palate event provides the beneficial effect of indicating, in advance of surgery, that UPPP will, more likely than not, be successful.

Data logging under the invention may be accomplished by any of a number of prior art methods. Heart rate, respiratory and snoring sounds, oxygen saturation of the blood and body position information, for instance, may be recorded as in U.S. Pat. No. 5,275,159, the disclosure of which is hereby incorporated by reference. Respiratory exertion may also be recorded from a strain gauge encircling the chest or abdomen of a sleeping subject. Under a preferred embodiment of the invention, a digital audio tape (DAT) recorder, Walkman AVLS, model TCD-D7 made by the Sony Corporation is used for logging audible and physiological events.

Figures 1, 2:
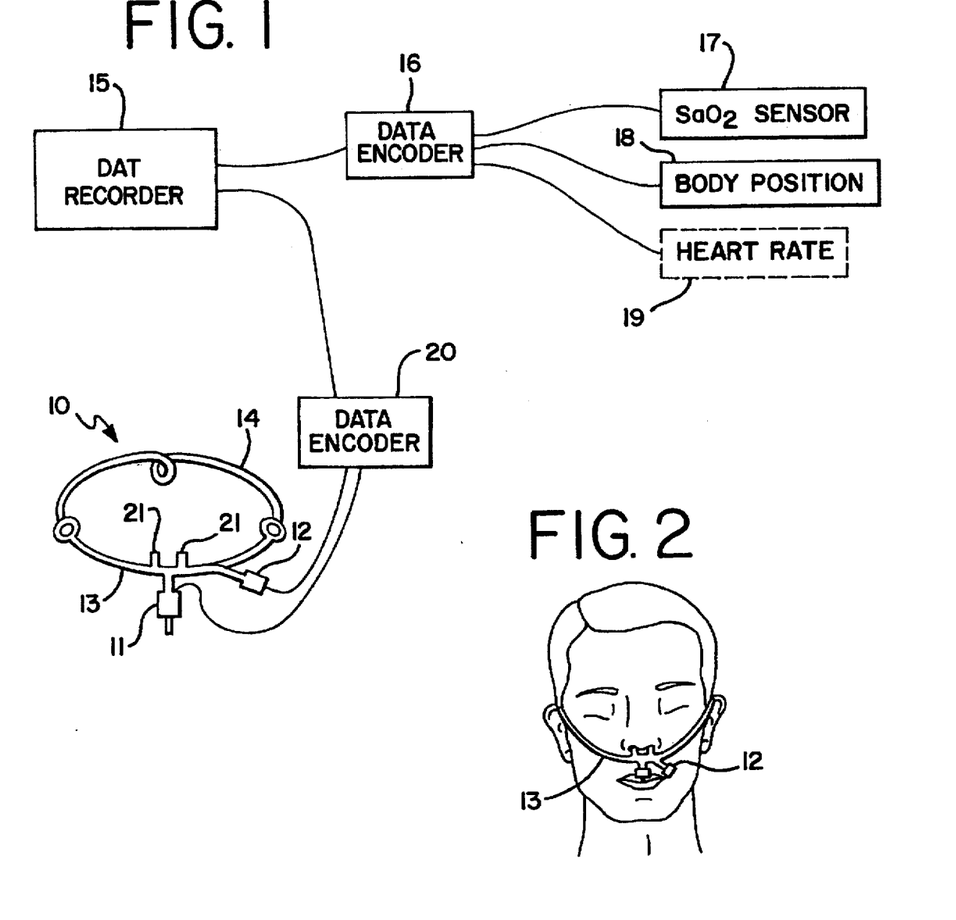
FIG. 1 is a block diagram illustrating a specific embodiment of a data recording apparatus in accordance with the invention.
FIG. 2 is a perspective view of a specific embodiment of an acoustic pick-up device on the head of a subject in accordance with the invention.

Turning now to FIG. 1, a two-channel DAT recorder 15 is shown in conjunction with a number of sensing devices 10, 17, 18 and 19. The $SaO_2$ sensor 17 is a conventional blood oxygen sensor that may be used to determine blood oxygen saturation based upon spectral absorption of a beam of light passing through a body appendage such as a finger or an earlobe. The body position sensor 18 may be a plastic tetrahedron with a metal ball inside and wires located at each apex of the tetrahedron and wherein body position is determined by the metal ball making contact with the wires at a particular apex of the tetrahedron. The optional heart rate detector 19 may be an acoustic detector. Other suitable alternative sensors for oxygen, position and heart rate are known in the art.

The sensor 10 in one embodiment is an acoustical pick-up device for respiration and snoring sounds originating from the nose or mouth of a sleeping subject. The mode of use of this sensor 10 may be more fully appreciated by reference to FIG. 2 where a strap 14 (not shown in FIG. 2) of the sensor 10 is placed around the head of the subject, thereby holding an acoustic pick-up tube 13 in proximate relation to the nose and mouth of the subject. Two short tubes 21 positioned at the nostrils of the subject (FIG. 2) conduct sounds from the nose of the sleeping subject through the pick-up tube 13 to a microphone 12. An optional second microphone 11 may detect respiratory and snoring sounds from the mouth of the subject. Alternatively, mouth and nasal sounds may be detected by microphone 12 by using a short tube in place of the microphone 11 to conduct sound from the mouth to the pick-up tube 13.

Optionally, a single microphone may be placed approximately 40 centimeters from the nose and mouth of a sleeping subject (or a single contact microphone may be placed on the throat of the sleeping subject) for the acoustical pick-up of respiratory and snoring sounds. The use of the sensor 10 or optional microphones has been determined to be more effective in detecting the sounds of snoring and/or airflow because of the proximity of the sound source to the sensor 10. Such detectors have been found useful under the invention in collecting apnea information as well as in providing improved signal-to-noise ratios.

Data encoders 16 and 20 are used to encode data for recording on each of the two channels of the DAT recorder 15. Data encoder 20 frequency limits microphones 11 and 12 to a bandwidth from 20–1250 Hertz and (where signals from two microphones are to be recorded on a single channel) may frequency shift (e.g., by modulating onto a 5 Khz carrier) the output of one of microphones 11 or 12 to a non-conflicting location within the 0–20 kilo-Hertz bandwidth DAT channel such that audio information from microphones 11 and 12 may be recorded and, later, separately recovered without loss of information. Other suitable encoding schemes are well known in the art.

Data encoder 16 may function similarly to data encoder 20 to encode data from the sensors 17, 18, 19, or use some other, simpler encoding process. Since the output of sensors 17–19 is analog and very low frequency, the information from the three sensors 17–19 may be either frequency shifted for storage on the DAT channel, as with encoder 20, encoded under a time division multiplex (TDM) format, or otherwise encoded to permit multiple sensor outputs to be recorded on a single channel. Alternatively, separate recording channels can be used to record each sensor output.

To maximize recording efficiency, the data encoder 20 may buffer 2–3 seconds of data and may compare a sound level at an input to the buffer with a number of threshold levels, including a first and second sound amplitude threshold values. (The first threshold may be referred to as an apnea threshold and the second threshold referred to as a snoring threshold). When the sound level rises above the first threshold, recording may be discontinued after some time period (e.g., 30 seconds). When the sound level falls below the first threshold (indicating breathing has stopped) recording may be restarted, resulting in 2–3 seconds of buffered data (occurring before the threshold transition) being recorded first. If the sound level stays below the first amplitude threshold for a third time period (e.g., 90 seconds) (indicating that the subject has awakened or the microphone has fallen off) the recorder may be again stopped.

Where the sound level exceeds the snoring threshold, recording is started after a fourth time period (e.g., 1 second) with, again, the buffered data recorded first. When the sound level falls below the snoring threshold, the recorder continues for a period allowing the sleeping subject to draw another breath. If the sound level does not again exceed the snoring threshold for a fifth time period (e.g., 45 seconds) recording may be again stopped.

After recording of physiological events for an appropriate period of sleep (e.g., 4–8 hours), the DAT recorder 15 is disconnected from the sleep subject and the results analyzed. To facilitate recovery of the recorded data, the DAT recorder 15 is interconnected (FIG. 3) with a general purpose computer (processor 30) through analog to digital converters (A/D's) 28, 29. Decoding (and separation) of individual microphone 11, 12 outputs may be accomplished digitally within the processor 30, as is well known in the art, or within optional decoders 26 or 27. Likewise, recovery of sensor 17–19 outputs may be accomplished within the processor 30 or within the decoder 26 or 27.

Figure 3:
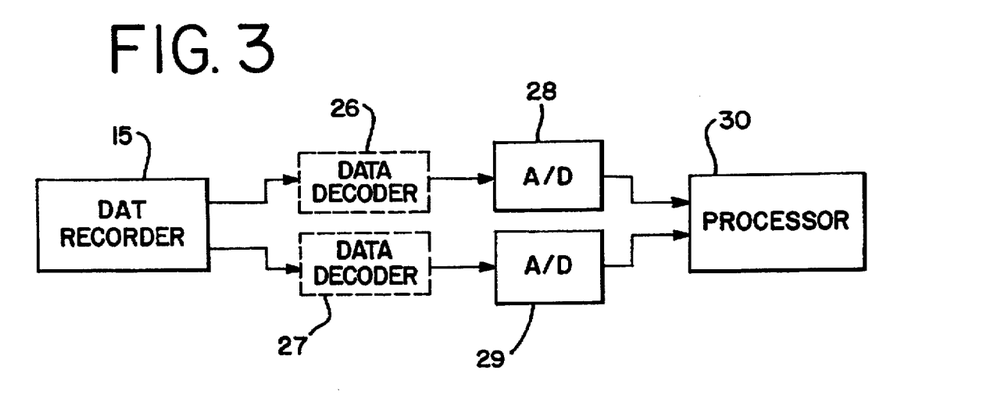
FIG. 3 is a block diagram of a specific embodiment of an apparatus for analyzing data from a subject in accordance with the invention.

Under one embodiment of the invention, recovery of data occurs at a very rapid rate by replaying the recorded data at 2–4 times recording speed into A/D's 28, 29 with frequency down-conversion occurring within the processor 30. Alternatively, a number of A/D's are provided and data from many recorders 15 are recovered in parallel by the processor 30 with the data from each recorder placed in a separate file for later analysis.

Upon transfer of the raw data into the processor 30, a first file containing audio information is created by the processor 30. The file is used by the processor to monitor the sound of the sleeping subject and identify breathing and snoring events. To facilitate data analysis, the processor 30 creates a sound envelope of breathing activity detected by each audio sensor.

To create a sound envelope, the processor 30 breaks the raw data into overlapping blocks (e.g., 300 samples per block with 100 samples at a first end overlapping a previous block and 100 samples at a second end overlapping a subsequent block). An absolute value of the largest sample of each block is stored in a reduced data file along with information detailing the location within the raw data of the largest sample of each data block.

Since the reduced data file contains a summary of the largest samples over a number of data blocks, the contents of the reduced data file may be displayed on a computer terminal as a sound envelope representation of the raw data file. Also, because of a 200:1 data reduction, several minutes of raw data may be displayed on the terminal as a sound envelope that is representative of the contents of the raw data file.

Under an embodiment of the invention drawn primarily to practicing the invention under a manual mode, an operator (not shown) of the processor 30 may use the sound envelope to identify likely episodes of apnea, hypopnea, or snoring. Using appropriate icons, the operator may scroll the sound envelope or raw data displayed on the terminal forward or backward to quickly identify profiles within the sound envelope or raw data indicating such events. An icon such as a time bar may be used in conjunction with scroll icons to quickly move from one area of recorded data to another. Split screen capability is also provided such that sections of this sound envelope (or raw data) may be compared with other sections of data. The operator may identify such episodes to the processor 30 by clicking and dragging a computer mouse across such an episode displayed on the monitor. Upon identifying an episode in such a manner, the processor 30 retrieves corresponding raw data and reconstructs the sound of the raw data through an audio speaker proximate the operator. Using such a method, an operator may differentiate between episodes of no breathing or inefficient breathing (apnea or hypopnea) and episodes of very quiet breathing. The operator may also use such an approach to differentiate between snoring and coughing or sneezing.

Alternatively, an operator may be trained to monitor the raw data through an audio speaker with the raw data played at 2–4 times the recorded speed. Upon identifying suspicious intervals, the operator may return the speed of play to a normal rate to hear a normal reproduction of a suspicious event.

In the case of apnea or hypopnea, the operator may identify such episodes by listening 100 to the sound and noting a duration of such an episode. Where episodes exceed some predetermined time length (e.g., 10 seconds) 102, the operator may cause that part of the sound envelope to be surrounded by a box (marker) and labeled with an appropriate character (e.g., "A" for apnea or "H" for hypopnea). The processor tabulates a total number of labeled boxes for the later generation of a summary.

In the case of snoring, the operator selects a section of data with an indication of snoring 103 and causes the processor 30 to do a frequency domain conversion (e.g., a fast fourier transfer) 104 on the selected data. [Fast fourier transformation may be accomplished by using the program provided on page 163 of *The Fast Fourier Transform* by E. Oran Brigham (Prentice-Hall 1974)]. The processor 30, upon transforming the data then displays the results for the benefit of the operator.

Fast fourier transformation (FFT) allows an operator to examine the frequency components of selected snoring events. Since different sections of the upper airway generate different signatures (frequency components), the identification 105 of those frequency components in the selected data provides a means of diagnosing the source of the snore. The most significant contributors to snoring in the upper airway (and the best candidate for UPPP) is the uvula and soft palate.

Snoring generated by the soft palate has a distinct pattern. A fundamental frequency of snoring generated by the soft palate is typically between 25–150 Hz and depends on the size of the uvula and soft palate, whether the snoring takes place during the inhalation or exhalation and whether the snoring was nasal or oral, or both. To evaluate fundamental and harmonic information within an episode (epoch), the operator characterizes the FFT data using a snore index 106 (e.g., where the episode is primarily of a fundamental and harmonics, a snore score of 1 is assigned and where fundamental or harmonics are negligible, a snore score of 5 is assigned). A snore index can be calculated as an average of the snore scores. The processor 30 tabulates the snore index and location as each episode is evaluated for purposes of the later generation of a summary report.

The fundamental frequency of snoring often changes during a snoring epoch (e.g., during inhalation or exhalation) because of changes in the size of the airway, air flow rate, etc. As a consequence, harmonics of the fundamental frequency are also present and changing. To accommodate and identify fundamental frequencies in a changing physical environment, the operator may be forced to reduce the affect of frequency changes in the search window. Narrowing the search window will often allow an episode that may originally have been a snore score 5 to be rated at a much lower snore score number. Narrowing the search window (reducing a terminal size of analogical data) offers such benefits by examining a much shorter term period where any shift in the fundamental frequency would presumably be much smaller. On the other hand, a narrow search window is to be avoided wherever possible because the use of a broad search window provides better resolution which is important at low frequencies.

It has been determined that an excellent candidate for UPPP is a subject with an identifiable fundamental and harmonics in each snoring epoch and very little energy in other frequencies (snore score=1). If the fundamental and harmonics are not easily identifiable, then the soft palate and uvula may not be a significant contribution to the snoring or that there may be other important sources of the snoring. (UPPP in such a case would be less successful in reducing snoring).

To simulate the effects of UPPP, the operator may eliminate 107 the fundamental frequency and harmonics within an episode, and simulate the effect through an audio speaker. The operator may eliminate the fundamental frequency and harmonics by individually selecting each frequency on the display of the processor 30 and activating a delete or attenuation function. Simulation of the effect is accomplished by performing an inverse fast fourier transform (IFFT) and routing the result to an audio speaker. A simulation of the effect of UPPP may then be determined by comparing decibel levels 108 of the original snores played back and the snores after deletion/reduction of fundamental/harmonics. Where differences in decibel level exceed some threshold value 109 (e.g., 17 db) a snore score of 1 would be indicated. A snore index of 1 is an indication of a soft palate event 111. Where the difference is some other threshold (e.g., less than 17 db), a higher snore index may be assigned indicating snoring of mixed origin 111.

Upon completion of analysis under the manual mode, a summary report may be generated by the processor 30. The summary report may include tabulations of such events as total number of apnea/hypopnea and snoring events detected within the data. Based upon the number of snore events a listing may be provided as to the number of snore events assigned to each snore index. Based on the distribution of snores among the snore index values a projection as to the site of snoring generation may be provided as part of this summary.

In another embodiment of this invention, sleep analysis (snoring, apnea, etc.), and report generation may be performed automatically by the processor 30. To analyze sleep disorders, the processor 30 identifies breathing events and searches for temporal gaps in such breathing events for apnea and hypopnea. The temporal gap between may be analyzed for apnea and hypopnea. Also, when the period between inhalation and exhalation (or intervening non-breathing event) have been identified, the analysis of snoring may be limited to more relevant areas.

Turning now to the identification of breathing events, a block diagram of the process may be found in FIG. 5. Reference will be made as appropriate in the explanation of blocks of FIG. 5 to corresponding locations source code in Appendix 1 (see microfiche appendix). References to Appendix 1 (see microfiche appendix) will be to alphanumeric characters (B1–B8) located in the left margins.

In the identification of breathing events, the data source is the reduced data file. After each sample is retrieved 200 from the reduced data file, the sample is compared 201 (source code location B1) to a breathing threshold level (breath.thresh). If the data sample exceeds breath.thresh, then a determination is made 202 of whether the data sample is the first of a breathing event (breath.beg=0) (source code location B2). If the sample is the first of a breathing event, then a breath counter is set to zero 203 (source code location B3). To measure the duration of the breath. After the breath counter is set to zero 203, or if the sample wasn't the first in a breathing event, then the breath counter is incremented 206 (source code location B4). A breath reset counter is also reset. A comparison is then made as to whether the current sample is the largest sample for that breathing event 208 (source code location B5). If the current sample is the largest sample, then a previous maximum is replaced by the current sample.

Through the blocks described 200–208, the breathing event detector (FIG. 5) measures the duration of the breathing event and locates a relative maximum for that breathing event. At the end of the breathing event (or during apnea) data samples no longer exceed the breath threshold and a different path is taken out of block 201.

After a breath is over (breath samples no longer exceed breath.thresh), the samples are each used to increment 204 (source code location B6) a breath reset counter. The contents of the breath reset counter are then compared with a threshold 205 (source code location B7) to determine if enough continuous samples below the breath threshold have been received to indicate that the breathing event is over. If so, the contents of the breath counter are then compared with a threshold 207 (source code location B8) to determine if the number of continuous samples exceeding the threshold were enough to consider the breathing event a full breath.

After the termination of breathing events, the breath threshold, an apnea threshold, and a hypopnea threshold are recalculated 211 (source code location B10) based upon an average 210 (source code location B9) of the last 10 breath maximas. Afterwards, or if the breathing event were determined to be a breath, then an apnea counter (apnea.count) is set equal to a current value of non-breath samples (breath.reset) and the processor 30 proceeds to look for apnea.

To this end and in a general sense, the processor 30 identifies gaps 100 with very little or no respiratory sound. Gaps are identified by comparing sound levels within a moving ten-second block of audio information with a threshold value. Where the sound threshold (apnea threshold) is not exceeded for ten continuous seconds 102 (and did not continue for more than 90 seconds), the processor 30 outputs indication 101 that the subject may have sleep apnea. In addition, the processor 30 may output an indication of blood oxygen level during the gap along with sleep position or may defer providing indication of sleep apnea unless the blood oxygen level falls below a threshold level.

During each breathing event (FIG. 5) whenever the breathing threshold (breath.thresh) is not exceeded for a number of samples exceeding a breath-reset threshold 205, the processor looks for apnea (FIG. 6). The processor 30 looks 300 for apnea by reading another data sample 301 (source code location AP1) and compares the data sample with an apnea threshold (apnea.thresh) 302 (source code location B1).

If the data sample does not exceed the apnea threshold, then a determination is made as to whether the sample is the beginning of an apnea interval 303 (source code location AP2). If the sample is the beginning of an apnea interval, an apnea counter (apnea.count) is set to zero 304 (source code AP3). Afterwards, or if the sample was not the beginning of an apnea event, an apnea counter (apnea.count) is incremented 305 (source code AP4) and an apnea reset counter (apnea.reset) is reset. For as long as the apnea period continues, the processor 30 processes data samples through blocks 301–305, each time incrementing the counter apnea.count.

At the end of an apnea period (the data sample exceeds apnea.thresh), the apnea reset counter is incremented 306 (source code AP5). When enough continuous samples exceeding the apnea threshold have been processed, such that the incrementing apnea reset value 306 exceeds a threshold 307 (source code AP6) a determination is made 308 that breathing has again begun.

After breathing again starts, a determination is made as to whether the duration of the apnea interval exceeded a threshold value 310 (source code AP7). If they were, the interval is an apnea event 311 (source code A8). If not, the interval was not apnea 313 (source code A8) and sets breathing parameters 312 (source code A8) to examine another breathing event.

Following the analysis of apnea, the processor 30 then analyzes snoring events. In a general sense and to be able to analyze snoring, the processor must be able to identify local maxima within the raw data.

To identify 103 local maxima, the processor examines a moving one-half second block of audio information for the highest relative magnitude audio event. To insure that the maxima is a significant event, the processor compares the maxima with adjacent audio information within the one-half second block to ensure that the maxima is at least twice the average of the magnitude of adjacent information within the one-half second block. In processing the raw data, the processor 30 creates a second file detailing the location of the local maxima within the raw data.

The raw data containing the local maxima is then fast fourier transformed 104 and may be stored in a third file by the processor 30. The previously identified local maximas are examined. Where the fast fourier transformed local maximas are comprised primarily of a fundamental frequency between 20–300 Hertz, and harmonics of the fundamental frequency, the processor 30 outputs 111 an indication that the snore or sound is substantially a soft palate event.

To facilitate the FFT in the illustrated embodiment, 1,024 data points (i.e., samples) centered around the local maxima are selected for transformation. Following transformation, a fundamental frequency is identified by finding a second set of maximas within the FFT data. Maximas within the FFT data are identified by calculating a smoothed FFT for each FFT data point. The smoothed FFT ($S_i$) is calculated as follows:

$$S_i = \frac{1}{2m_i + 1} \sum_{i-m_i}^{i+m_i} F_i$$

where "i" is the frequency, $F_i$ is the FFT amplitude at the "ith" frequency, $M_i$ is the smoothing order (e.g., 4), and 20 Hz<i<300 Hz. To determine a maxima each $S_i$ is compared with its neighbors on each side. $S_i$ is a maxima if $S_i$ is greater than or equal to $S_j$ for all $i-m_2<j<i+m_2$ where $m_2$ is a range of evaluated FFT data points (e.g., 10). An actual maxima is determined around each frequency of $S_j$ ($i_{sj}$) for one data point is less than or equal to $S_j$ is less then or equal to $m_2$ data points. An FFT point is a maxima ($F_{imax}$) if $F_{imax}$ is greater than or equal to $F_{ik}$ for any $i_k$ where $i_{sj}-m_2<i_k<i_{sj}+m_2$.

Insignificant FFT maximas are eliminated by considering surrounding FFT data points. If the magnitude of surrounding FFT points do not drop to some proportional value (e.g., ⅓) within $M_3$ FFT points (e.g., 10) and stay below the proportional value for an additional $M_4$ FFT points (e.g., 40), then the FFT maxima is dropped from consideration. To state the premise in another manner $F_{imax}$ is a significant maxima if $F_{imax}$ is >3$F_i$; where $i_{max}-M_3-M_4<i<i_{max}-M_3$.

Once the insignificant FFT maximas have been eliminated, the remaining FFT maximas are ordered in terms of increasing frequency. An attempt is made to group FFT maximas in terms of a fundamental frequency and its harmonics. The first FFT maxima of the ordered group, at the lowest fundamental frequency $i_1$, is used to identify harmonics through the use of the equality $i_k=i_1*l+/-\delta$ where $i_1$ is a harmonic of $i_1$, l is an integer greater than one, and $\delta$ is an allowed error (e.g., 1). Any FFT maximas at a frequency of $i_1$ and $i_k$ is considered part of a harmonic group which included the fundamental frequency and any harmonics.

The process can be repeated for the next fundamental frequency (FFT maxima) of the remaining FFT maximas within the ordered group. The FFT maxima at the next highest frequency $i_2$ (and multiples) become part of a second harmonic group. The process may be repeated again and again until more FFT maximas have all been included in some harmonic group.

It has been noted in some cases that a fundamental frequency may not be included within the original group of FFT maximas. When this happens, it will not be possible to group some FFT maximas of the ordered group of FFT maximas within a harmonic group. One means of solving this problem is to divide the frequency of the lowest frequency FFT maxima of the remaining ordered group by 2 (or 3) and use the result as a fundamental frequency. Using such a procedure can make it possible to place more FFT maximas within a harmonic group.

Once the FFT maximas have been placed into harmonic groups, the harmonic groups having fundamental frequencies in the range of from 20–300 Hz are identified 105. Since it has been determined that snoring having fundamental frequencies in the range of from 20–300 Hz is an event primarily associated with the structures of the soft palate and uvula and since UPPP can be effective in reducing snoring produced by the uvula, the determination of the contribution of sound produced by the uvula provides an important benefit.

To evaluate the sound contribution of the soft palate and uvula, the identified 105 harmonic groups having fundamental frequencies in the range of from 20–300 Hz are subtracted 107 from the original sounds of snoring and the decibel reduction in volume of the FFT residual maxima evaluated 108. If it is noted that the reduction exceeds some threshold (e.g., 17 db) 109, then the site of snoring generation is the velum and the subject may be a good candidate for UPPP 111.

To facilitate a comparison of sound levels, the FFT maximas (data points) of the identified harmonic group are subtracted from the original fast fourier transformed data and the result is optionally stored in a fourth file. To obtain a decibel comparison between the FFT points in the third and fourth files, a weighing factor must be associated with each of the FFT values within each data file based upon frequency. Through the use of the weighing, the loudness of the third and fourth files can be compared. Given an FFT value of $F_i$ (0<i<N-1 and N is the order of the FFT volume), the effective loudness L(f) in Db can be determined by evaluation of the function as follows:

$$L(f) = 10\log_{10} \sum_{i=0}^{N-1} W_i F_i$$

If the loudness of the original data is greater than 50 phons, then relative weight values for a range of frequencies can be described as follows:

W1000 Hz=W100 Hz×(3.2)
W500 Hz=W100 Hz×(2.5)
W200 Hz=W100 Hz×(1.8)
W100 Hz=W 50 Hz×(1.8)

To determine an absolute set of weight values, an arbitrary weight value may be chosen for a particular frequency (e.g., W 100 Hz=1) and weight values determined for other frequencies either directly from the above equations or by extrapolation.

Alternatively, linear weight values may be used. Other weighting schemes (e.g., logarithmic, et cetera) may also be used in accordance with the invention.

In one embodiment of this invention, the above process is more fully described in FIG. 6. Following FFT 400, a density function is calculated for low frequency components of the FFT of from 20–350 HZ. The density function is calculated 401 (source code R1) in accordance with the invention by integrating the FFT across the frequency range (20–350 HZ) and dividing by the number of frequency components integrated. Likewise, a density function is calculated for mid-frequencies (350–750 HZ) 402 (source code R2) and for high frequencies (750–1200 HZ) 403 (source code R3).

The density functions are then compared 404 (source code R4). If the low frequency density function is greater than the mid-frequency, and/or the mid-frequency is greater than the high-frequency density, then the event is determined to be snoring 405. If not, then the event is not a snore 407. (Corresponding references HA and 406, HC and 418, H5 and 419, HB and 420, CL13 and 433, and EMULATE UPPP and 435 indicate connection only). Another way to detect whether a breathing event is a snore, is to use another microphone not in the air flow path and to use a simple amplitude threshold criteria to identify snoring.

Following a determination that an event is snoring, a set of threshold values are calculated 408 (source code H1). An FFT sample is then loaded 411 (source code H2) and compared with a threshold value 413 (source code H3) to insure that the FFT sample is not outside a range of interest.

If the FFT sample is within the range of interest, then a determination 414 (source code H4) is made as to where it falls within the spectrum (low, medium, or high) and the FFT sample is then compared 415–417 with an appropriate threshold value L.TH1, MTH1, or H.TH1) to eliminate insignificant peaks.

If the FFT sample is greater than the relevant threshold, then a determination is made 421 as to whether the sample is the first FFT sample of a new maxima 423. If it is the first FFT sample of a new maxima, then the counter harm.reset is reset.

If the FFT sample is not the first FFT sample of a maxima, then a current harm.reset value is compared with a threshold value 424 (source code H6) and incremented 427 (source code H8) before being compared a second time with the threshold value 429 (source code H9). If in either comparison 426, 429 it is determined that the value of harm.reset exceeds the threshold (harm.term) the FFT sample is outside the range to be considered and is not a maxima 427 and the parameters are reset 428 (source code H7) for consideration of another maxima. If harm.reset value of an FFT sample were less than the value of harm.term, then the FFT sample will be retrieved under pre-existing parameters.

A sample number, "i", is incremented 409 and the incremented sample number compared 410 to an event size (1024 samples). If the sample number is less than the event size, then another sample from the same maxima is retrieved 411. If not, the processor 30 proceeds 412 to look for fundamentals and harmonics.

The processor first tests if one of the identified frequencies was a maxima 430 (source code C11) indicating the presence of a fundamental frequency. If no fundamental is found, the event is rated 431 (source code CL8) as a snore index 5 and the result reported 444 (source code CL13) to a summary file.

If a maxima is found 430 the processor 30 determines the fundamental frequency to be the first maxima frequency 432 (source code CL2). The processor 30 then loads a next maxima 434 (source code CL3) and determines 436 (source code CL4) if it is an integer multiple of the fundamental. If so, another maxima is loaded 434 and considered 436. If not, the processor attempts to determine 437, 438 whether the first maxima is a multiple of the fundamental.

Follow the identification (grouping) of fundamentals and harmonics 106, the processor emulates the effect of a UPPP. The processor first sets 439 (source code CL8) a frequency width equal to the fundamental frequency divided by 4. The processor then zeros 440 (source code CL9) all FFT harmonic values closer than the calculated frequency width to the fundamental and the harmonics frequency. An FFT is then calculated 441 (source code CL10) of a simulated UPPP to the original FFT ratios. The ratios are then used to determine 442 (source code CL11) a source index which is then corrected 443 (source code CL12) before saving and printing 444 (source code CL13) a summary report. A normalized snore index for each snore index classification (1–5) may be calculated by squaring the snore index for each event of each class, summing the squared indexes of each class, and dividing the summed indexes of each class by the summed total of all classes.

The summary may include a list of the dominant fundamental frequencies as well as secondary fundamentals detected. An estimation of the relative energy in the fundamental (and harmonics) as opposed to all frequencies, may be provided. The energy content of certain fundamental frequencies, compared to appropriate threshold values, may be used as an indicia of snoring from multiple sources or, otherwise, as an indicia of a velum snore. The relative energy content of fundamentals and harmonics of from 20–300 Hz and harmonics against total energy of sound may be calculated and included in the summary as a velum snore index.

The summary may identify the soft palate of the subject as the source of the snoring and label the snoring as a velum snore when the sound is predominantly of a fundamental frequency of from 20–150 Hz and harmonics, and a non-velum snore involving the tonsils when the fundamental frequency is above 130 Hz. Where the FFT indicates a diffuse sound, the summary may indicate a non-velum snore implicating the pharyngal and nose or otherwise a mixed source when the snoring contains an indicia of multiple sources, such as when the energy of fundamental frequencies and harmonics compared to total sound is below a threshold. The summary may also provide an indication of the different types of events occurring during a sleep interval by indicating a velum snore index from the total velum, non-velum, and mixed snores during a time interval.

In another embodiment of the invention other methods are used to identify the presence of harmonic patterns based in the 20–300 Hz range. One method involves finding a first value "d" and a second value "a" such that during the snoring event the wave amplitude in the time domain will comply with the equation as follows:

$$S(t)=aS(t-d)+\delta$$

where "d" is the cycle time of the fundamental frequency in seconds, "a" is an amplitude that is usually close to 1 that changes very slowly, and "δ" is an allowed error. If "d" is greater than 30 milliseconds, then "d" is the fundamental frequency wave length in seconds. If "d" is much less than 30 milliseconds, then "d" will be centered around a harmonic wave length and the equation will be valid for only subsections of the snoring event.

The foregoing specification describes only the preferred embodiments of the inventions as shown. Other embodiments besides the ones described above may be articulated as well. The terms and expressions, therefore, serve only to describe the invention by example only and not to limit the invention. It is expected that others will perceive differences which, while differing from the foregoing, do not depart from the spirit and scope of the invention herein described and claimed.

In another embodiment of the invention, data analysis is performed on data received directly from the subject by a processor 30 located near the sleeping subject. Data may also be recorded for later evaluation.

I claim:

1. A method of detecting and analyzing sleep disorders comprising the steps of:
   monitoring sound produced by a sleeping subject through a sensor proximate the sleeping subject;
   continuously recording the monitored sound;
   identifying snoring within the recorded sound;
   analyzing the identified snoring to locate upper airway structural sources generating the snoring; and
   identifying a soft palate of the sleeping subject as the source of the snoring and as a velum snore when the snoring is substantially of a fundamental frequency between a lower and upper threshold and harmonics of the fundamental frequency.

2. The method as in claim 1 wherein the step of analyzing the monitored sound for respiratory system structural sources of snoring further comprising the step of identifying a set of tonsils or other non-velum sources of the sleeping subject as the source of the snoring, and as a non-velum snore, when the snoring is substantially of a fundamental frequency greater than an upper threshold and harmonics of the fundamental frequency.

3. The method as in claim 2 wherein the step of analyzing the monitored sound for respiratory system structural sources of snoring further comprises the step of identifying one of a pharyngal and nose as the source of snoring, and as a non-velum snore, when a fourier transform of the recorded sound indicates a diffused sound source, and otherwise a mixed snore when the snoring contains an indicia of multiple sources.

4. The method as in claim 2 further comprising the step of selecting intervals of data from the raw data file and displaying the selected interval under an expanded format on a computer monitor.

5. The method as in claim 2 further comprising the step of graphically outputting a distribution of snoring classifications.

6. The method as in claim 2 further comprising the step of simulating an effect of surgery by reproducing the recorded sound without fundamental frequencies and harmonics of the fundamental frequencies.

7. The method as in claim 1 further comprising the step of determining a relative sound contribution of fundamental frequencies and harmonics.

8. A method of detecting and analyzing sleep disorders comprising the steps of:
   monitoring sound produced by a sleeping subject through a sensor proximate the sleeping subject;
   continuously recording the monitored sound;
   identifying snoring within the recorded sound;
   analyzing the identified snoring to locate upper airway structural sources generating the snoring;
   evaluating the recorded sound using frequency domain methods; and
   using a plurality of temporal sizes of data for frequency analyzing the snoring.

9. A method of detecting and analyzing sleep disorders comprising the steps of:
   monitoring sound produced by a sleeping subject through a sensor proximate the sleeping subject;
   continuously recording the monitored sound;
   identifying snoring within the recorded sound;
   analyzing the identified snoring to locate upper airway structural sources generating the snoring;
   generating a raw data file and a reduced file; and
   tabulating and outputting a number indicating total velum, non-velum, and mixed snore during a time interval.

10. The method as in claim 9 further including the step of calculating a velum snore index from the total velum, non-velum, and mixed snore during a time interval.

11. The method as in claim 9 further comprising the step of projecting a likelihood of success of uvulopalatopharnygoplasty based upon at least one of the calculated total velum, non-velum, and mixed snore per time period, and/or the velum snore index.

12. The method as in claim 9 further comprising the step of displaying a raw data file or a reduced data file of the recorded sound on a computer monitor.

13. The method as in claim 12 further comprising the step of marking displayed raw data and frequency domain transforming the marked raw data into a second display window.

14. The method as in claim 12 further comprising the step of marking displayed data and outputting the data to an audio speaker for verification of the event as one of breathing, apnea, hypopnea and snoring.

15. The method as in claim 12 further comprising the step of deleting markers of selected data intervals.

16. The method as in claim 12 further comprising the step of manually identifying the structural source of the snoring of the classified data intervals.

17. The method as in claim 16 further comprising the step of reducing the digitized monitored sound and storing the reduced data file in conjunction with selected portions of the digitized monitored sound.

18. The method as in claim 9 further comprising the step of manually classifying data intervals as one of breathing, apnea, hypopnea, and snoring.

19. The method as in claim 9 further comprising the step of randomly accessing the raw data file and scrolling one of the raw data and data envelope in either a forward or backwards direction on a computer monitor.

20. The method as in claim 9 further comprising the step of randomly accessing the reduced data file and one of expanding and scrolling and, upon occasion, reproducing a corresponding portion of the raw data file in either identical interval size or expanded interval size and scrolling in either a forward or reverse direction on a computer monitor.

21. A method of detecting and analyzing sleep disorders comprising the steps of:

monitoring sound produced by a sleeping subject through a sensor proximate the sleeping subject;

continuously recording the monitored sound;

identifying snoring within the recorded sound;

analyzing the identified snoring to locate upper airway structural sources generating the snoring; and comparing the monitored sound with a first recording threshold level and deactivating the recorder when the monitored sound exceeds the first threshold levels for at least a first time period and otherwise reactivating recording when the monitored sound does not exceed the threshold for a second time period.

22. The method as in claim 21 further comprising the step of comparing the monitored sound with a second threshold and reactivating the recorder when the monitored sound exceeds the first and second thresholds for a third time period and deactivating the recorder when the monitored sound exceeds the first threshold but not the second for a fourth time period.

23. A method of detecting snoring comprising the steps of:

monitoring sound produced by a sleeping subject through a sensor proximate the sleeping subject;

recording the monitored sound;

visually observing a sound signal of the recorded sound on a display;

selecting a section of the displayed recorded sound; and outputting the selected section through an audio transducer.

24. A method of detecting apnea comprising the steps of:

monitoring sound produced by a sleeping subject through a sensor proximate the sleeping subject;

recording the monitored sound;

visually observing a sound signal of the recorded sound on a display;

selecting a section of the recorded sound; and outputting the selected section through an audio transducer.

25. A method of detecting and analyzing sleep disorders comprising the steps of:

monitoring sound produced by a sleeping subject through a sensor proximate the sleeping subject;

continuously recording the monitored sound;

identifying snoring within the recorded sound;

analyzing the identified snoring to locate upper airway structural sources generating the snoring; and identifying a soft palate of the sleeping subject as the source of the snoring, as a velum snore, when the snoring is substantially of a fundamental frequency below a threshold and harmonics of the fundamental frequency.

* * * * *